(12) United States Patent
Kodoi et al.

(10) Patent No.: US 9,185,926 B2
(45) Date of Patent: Nov. 17, 2015

(54) HIGH-ZINC YEAST EXTRACT, METHOD OF PRODUCING SAME AND AGENTS AND FOODS CONTAINING SAME

(71) Applicant: ORIENTAL YEAST CO., LTD., Tokyo (JP)

(72) Inventors: Rie Kodoi, Tokyo (JP); Takayasu Takahashi, Tokyo (JP); Osamu Oka, Tokyo (JP); Hiromi Urasaki, Tokyo (JP)

(73) Assignee: ORIENTAL YEAST CO., LTD., Tokyo (JP)

(*) Notice: Subject to any disclaimer, the term of this patent is extended or adjusted under 35 U.S.C. 154(b) by 0 days.

(21) Appl. No.: 14/243,609

(22) Filed: Apr. 2, 2014

(65) Prior Publication Data

US 2014/0212571 A1 Jul. 31, 2014

Related U.S. Application Data

(63) Continuation of application No. PCT/JP2012/074930, filed on Sep. 27, 2012.

(30) Foreign Application Priority Data

Oct. 4, 2011 (JP) ................................. 2011-220309

(51) Int. Cl.
| | |
|---|---|
| A23L 1/28 | (2006.01) |
| A23L 1/272 | (2006.01) |
| A61K 36/064 | (2006.01) |
| A23L 1/30 | (2006.01) |
| A23L 1/304 | (2006.01) |
| A23L 1/212 | (2006.01) |
| A23L 3/3508 | (2006.01) |
| A23L 3/3571 | (2006.01) |
| A23B 7/154 | (2006.01) |

(52) U.S. Cl.
CPC . *A23L 1/28* (2013.01); *A23B 7/154* (2013.01); *A23L 1/2123* (2013.01); *A23L 1/272* (2013.01); *A23L 1/304* (2013.01); *A23L 1/3018* (2013.01); *A23L 1/3045* (2013.01); *A23L 3/3508* (2013.01); *A23L 3/3571* (2013.01); *A61K 36/064* (2013.01)

(58) Field of Classification Search
CPC ....... A23L 1/28; A23L 1/272; Y10S 530/824; C12N 1/16; C12N 1/18; C12N 1/063; C12N 2500/74

See application file for complete search history.

(56) References Cited

U.S. PATENT DOCUMENTS 7,399,475 B1 7/2008 Grabitz

FOREIGN PATENT DOCUMENTS

| CN | 1615680 | | 5/2015 |
|---|---|---|---|
| DE | 10258129 | * | 6/2004 |
| FR | 2884691 | * | 10/2006 |
| JP | 09-124438 | | 5/1997 |
| JP | 9-124438 | | 5/1997 |
| JP | 2001-149049 | | 6/2001 |
| JP | 2005-102618 | | 4/2005 |
| JP | 2006-217914 | | 8/2006 |
| JP | 3810836 | | 8/2006 |
| WO | 00/64417 | | 11/2000 |
| WO | 2005/087024 | | 9/2005 |

OTHER PUBLICATIONS

English Translation for DE 10258129 published Jun. 2004.*
English Translation for FR 2884691 published Oct. 2006.*
English Translation for JP 09-124438 published May 1997.*
"Dietary Reference Intakes for Japanese 2010," Ministry of Health, Labour and Welfare, the report from the Scientific Committee of "Dietary Reference Intakes for Japanese", published by DAI-ICHI SHUPPAN Co. Ltd., p. 227-230 (Sep. 20, 2009), English translation provided.
Sugimoto, "Transition of yeast extract production method (I)—from the trend of patent applications in Japan—," New Food Industry 1994, vol. 36, No. 10, pp. 41-48, English translation provided.
Supplementary European Search Report dated Jun. 12, 2015 for corresponding European patent application EP 12838349 (7 pages total).
Chinese Office Action for the corresponding Chinese application No. 201280049120.X dated Sep. 6, 2015, English translation (35 pages).
Xiaohong Wang: "Functional Food Additive: Production Characteristics and Uses of Yeast Autolysate"; Institute of Foodgrain Science of Heilongjiang, Oct. 2000, 8 pages.
"Wine Production Technology"; Beer Production Technology, Engligh translation, 4 pages.

* cited by examiner

*Primary Examiner* — Anthony Weier
(74) *Attorney, Agent, or Firm* — Hamre, Schumann, Mueller & Larson, P.C.

(57) ABSTRACT

A method for producing a high-zinc-content yeast extract, including extracting the high-zinc-content yeast extract by suspending zinc-containing yeast into a solution containing a carboxylic acid, a carboxylic acid salt, or both thereof to thereby obtain a suspension liquid, and separating a solid component and a liquid component of the suspension liquid; the high-zinc-content yeast extract; food; and an agent for maintaining and restoring a green color of vegetables.

11 Claims, 7 Drawing Sheets

Ex. 4　　Comp. Ex. 3-1　Comp. Ex. 3-2　Comp.Ex. 3-3

Ex. 4　　Comp. Ex. 3-1　Comp. Ex. 3-2　Comp.Ex. 3-3

HIGH-ZINC YEAST EXTRACT, METHOD OF PRODUCING SAME AND AGENTS AND FOODS CONTAINING SAME

CROSS-REFERENCE TO RELATED APPLICATION

This application is a continuation application of International Application PCT/JP2012/074930 filed on Sep. 27, 2012 and designated the U.S., the entire contents of which are incorporated herein by reference.

BACKGROUND OF THE INVENTION

1. Field of the Invention

The present invention relates to a method for producing a high-zinc-content yeast extract which contains zinc derived from a natural product in a high concentration, which is excellent in water-solubility, which can ameliorate zinc deficiency-associated dermatitis and dysgeusia; and which can be suitably used as an oral or tube feeding composition (e.g., a liquid food) or a food material; the high-zinc-content yeast extract; food (e.g., a liquid food and a beverage) containing the high-zinc-content yeast extract; and an agent for maintaining and restoring a green color of vegetables.

2. Description of the Related Art

According to the data recently published by Ministry of Health, Labour and Welfare, the daily zinc requirement is about 10 mg in adult males, and about 8 mg in adult females. Zinc deficiency in vivo has been well known to cause dermatitis and dysgeusia, and potentially causes chronic diarrhea, hypoalbuminemia, pancytopenia, growth disorder, and gonadal dysgenesis (see "Dietary Reference Intakes for Japanese 2010," Ministry of Health, Labour and Welfare, the report from the Scientific Committee of "Dietary Reference Intakes for Japanese", published by DAI-ICHI SHUPPAN Co. Ltd., p. 227-230 (2009 Sep. 20)). Therefore, there is a need to develop a safe food material for a liquid food or a beverage which allows for efficient ingestion and absorption of zinc into a living body, and which can ameliorate zinc deficiency-associated dermatitis and dysgeusia. Yeast has been utilized as a food material by human since a long time ago. For example, brewer's yeast has been utilized as a source of supply of dietary fiber, vitamin, or mineral. Especially, yeast into which zinc has been uptaken or extract thereof is thought to be available as a safe zinc-enriched food material.

However, in conventional zinc-containing yeast, a distinctive odor such as a yeast odor and a distinctive taste such as a yeast taste are insufficiently reduced, making it unsuitable as a food material. The conventional zinc-containing yeast is water-insoluble, so that turbidity and precipitation are caused when it is added to food. As a result, the conventional zinc-containing yeast cannot be used in, especially, a soft drink, which is problematic.

In order to solve the above problems, there has been proposed a zinc-containing yeast extract which is extracted from the zinc-containing yeast. Extraction of a yeast extract from mineral-containing yeast (e.g., zinc-containing yeast) has been performed by, for example, the following methods: (1) a hot-water extraction method, (2) an autolysis method, (3) an enzymolysis method, and (4) a hydrolysis method with hydrochloric acid or sulfuric acid (see Hiroshi Sugimoto, "Transition of yeast extract production method (I)—from the trend of patent applications in Japan—," New Food Industry 1994, Vol. 36, No. 10, p. 41-48). However, the methods of (1) to (3) have a problem of a low mineral recovery rate (zinc extraction rate). The methods of (2) and (3) have a problem that a yeast odor and an extract taste remain in the resultant yeast extract. The method of (3) has problems of a high cost and a residual enzyme in the resultant yeast extract. The method of (4) has a problem that a counter ion of the mineral (e.g., chlorine ion or sulfate ion) may remain in the resultant yeast extract, making the yeast extract unsuitable for a food material.

Metals such as zinc have a possibility to be used for restoring a green color of vegetables. It has been known that the green color of vegetables (including processed vegetables) is disappeared due to a change of chlorophyll during processing (e.g., blanching, heat sterilization, drying, fermentation, and salting) and during storage. Therefore, in, especially, food processing industry, there has been a demand to maintain the green color of vegetables for a long period of time, because maintenance of the green color of vegetables affects shelf life of food and processed products thereof. However, a safe metal-containing material capable of being added to food has not been known, and maintenance of the green color of vegetables for a long period of time has not been achieved.

Therefore, there has been demanded a method for efficiently producing a high-zinc-content yeast extract which has sufficiently reduced distinctive odor (e.g., yeast odor) and distinctive taste (e.g., yeast taste), and which is suitable as a safe food material; the high-zinc-content yeast extract; food (e.g., a liquid food and a beverage) containing the high-zinc-content yeast extract; and an agent for maintaining and restoring a green color of vegetables.

SUMMARY OF THE INVENTION

The present invention aims to meet the demand, break the status quo, solve the existing problems, and achieve the following objects. That is, an object of the present invention is to provide a method for producing a high-zinc-content yeast extract which contains zinc derived from a natural product in a high concentration, which is excellent in water-solubility, which does not impair appearance of food containing it, which can be suitably used as an oral or tube feeding composition (e.g., a liquid food or a beverage) and a food material, and which does not impair a flavor of food containing it the high-zinc-content yeast extract; food; and an agent for maintaining and restoring a green color of vegetables.

Means for Solving the Problems are as Follows

<1> A method for producing a high-zinc-content yeast extract, including: extracting the high-zinc-content yeast extract by suspending zinc-containing yeast into a solution containing a carboxylic acid, a carboxylic acid salt, or both thereof to thereby obtain a suspension liquid, and separating a solid component and a liquid component of the suspension liquid.

<2> The method for producing the high-zinc-content yeast extract according to <1>, wherein a total amount of the carboxylic acid and the carboxylic acid salt is 0.2 mol or more relative to 1 mol of zinc contained in the yeast.

<3> The method for producing the high-zinc-content yeast extract according to <1> or <2>, wherein the carboxylic acid is a bivalent or higher carboxylic acid, and wherein the carboxylic acid salt is a bivalent or higher carboxylic acid salt.

<4> The method for producing the high-zinc-content yeast extract according to any one of <1> to <3>, wherein the carboxylic acid is a trivalent carboxylic acid, and wherein the carboxylic acid salt is a trivalent carboxylic acid salt.

<5> The method for producing the high-zinc-content yeast extract according to any one of <1> to <4>, including, prior to the extracting, hot-water treating the yeast by suspending the yeast into hot-water of 60° C. to 120° C. to thereby obtain a suspension liquid, and separating a solid component and a liquid component of the suspension liquid.

<6> The method for producing the high-zinc-content yeast extract according to <5>, wherein, in the hot-water treating, a phosphoric acid salt is added to the hot-water.

<7> The method for producing the high-zinc-content yeast extract according to any one of <1> to <6>, wherein a pH of the suspension liquid in the extracting is 3.0 to 10.0.

<8> The method for producing the high-zinc-content yeast extract according to any one of <1> to <7>, wherein the separating the solid component and the liquid component of the suspension liquid in the extracting is performed through filtration.

<9> The method for producing the high-zinc-content yeast extract according to any one of <5> to <8>, wherein the separating the solid component and the liquid component of the suspension liquid in the hot-water treating is performed through filtration.

<10> A high-zinc-content yeast extract, including:
  0.4% by mass or more of zinc derived from a yeast fungus body,
  wherein a turbidity is 0.10 or less in terms of absorbance at a wavelength of 660 nm (O. D. 660) when 1 g of the high-zinc-content yeast extract is dissolved or dispersed into 100 mL of water.

<11> The high-zinc-content yeast extract according to <10> produced by the method for producing the high-zinc-content yeast extract according to any one of <1> to <9>.

<12> The high-zinc-content yeast extract according to <10> or <11>, wherein the yeast is edible yeast.

<13> The high-zinc-content yeast extract according to <12>, wherein the edible yeast is at least one selected from the group consisting of baker's yeast, brewer's yeast, wine yeast, sake yeast, and miso and soy sauce yeast.

<14> The high-zinc-content yeast extract according to <12>, wherein the edible yeast is *Saccharomyces cerevisiae*.

<15> The high-zinc-content yeast extract according to any one of <10> to <14>, wherein the high-zinc-content yeast extract is added to food.

<16> The high-zinc-content yeast extract according to <15>, wherein the food is a liquid food or a soft drink.

<17> Food, including:
  the high-zinc-content yeast extract according to any one of <10> to <16>.

<18> An agent for maintaining and restoring a green color of vegetables, including:
  the high-zinc-content yeast extract according to any one of <10> to <14>.

The present invention can solve the existing problems, and can provide a method for producing a high-zinc-content yeast extract which contains zinc derived from a natural product in a high concentration, which is excellent in water-solubility, which does not impair appearance of food containing it, which can be suitably used as an oral or tube feeding composition (e.g., a liquid food or a beverage) and a food material, and which does not impair a flavor of food containing it the high-zinc-content yeast extract; food; and an agent for maintaining and restoring a green color of vegetables.

DETAILED DESCRIPTION OF THE INVENTION

Production Method of High-Zinc-Content Yeast Extract

Figure 1:
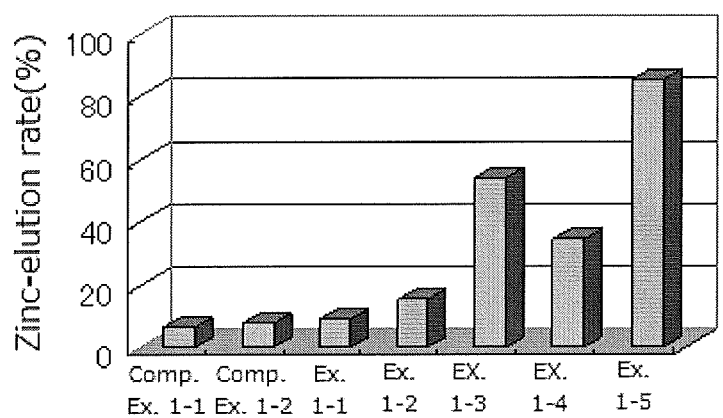
FIG. 1 is a graph illustrating zinc-elution rates with pure water, sodium chloride, and each carboxylic acid salt in Example 1 and Comparative Example 1.

A method for producing a high-zinc-content yeast extract of the present invention includes an extraction step; and, if necessary, further includes other steps such as a hot-water treatment step and a drying step.

<Extraction Step>

The extraction step is a step of suspending zinc-containing yeast into a solution containing a carboxylic acid, a carboxylic acid salt, or both thereof to thereby obtain a suspension liquid, and separating a solid component and a liquid component of the suspension liquid. The extraction step results in a high-zinc-content liquid component (extract).

<<Yeast>>

The yeast is not particularly limited and may be appropriately selected depending on the intended purpose, as long as it contains zinc in its fungus body. A zinc-content in the yeast is preferably high as possible in the case where the high-zinc-content yeast extract is used as a zinc-enriched food material. However, from the viewpoint of an efficient production of the high-zinc-content yeast extract, the zinc content is preferably 0.06% by mass to 10% by mass, more preferably 5% by mass to 10% by mass, relative to dry mass of fungus body.

The zinc content, as used herein, refers to an amount of zinc contained in a yeast fungus body. For example, the zinc content is preferably kept at a high level even after washing, for example, in the case where a fungus body is washed with water. In such a yeast, zinc is not removed and remains within the fungus body even after washing, so that the zinc is derived from the fungus body and is highly safe. Therefore, in the case where the hot-water treatment (washing) is performed for reducing an odor and a taste which are distinctive of yeast, the yeast extract does not impair a taste of food containing it, and contains the zinc in a high concentration. As a result, the yeast extract is suitable as a food material.

Note that, the zinc content in the yeast can be measured by known methods such as an atomic absorption spectrometry.

The zinc-containing yeast may be produced by culturing yeast in a zinc-containing culture medium to thereby allow zinc to be uptaken into a fungus body of the yeast; or may be produced by suspending yeast into a solution containing 50 ppm by mass or more of zinc, followed by agitating and/or shaking (see, for example, Japanese Patent Application Laid-Open (JP-A) No. 08-332082); or may be a commercially available product. Examples of the commercially available product include MINERAL YEAST ZN5 and MINERAL YEAST ZN5-F (both manufactured by Oriental Yeast Co., Ltd.). An amount of zinc to be added to the culture medium is not particularly limited and may be appropriately selected depending on the intended purpose, but it preferably achieves both of a high zinc utilization rate (uptake rate of zinc into a fungus body) and a high yield based on sugar (growth rate).

Note that, a type of zinc to be added, a type of a culture medium, and a culturing condition are not particularly limited and may be appropriately selected depending on the intended purpose.

The zinc-containing yeast may be further pulverized so that unpulverized fungus body cannot be observed under a microscope. Even when the yeast is pulverized yeast, the zinc content in the yeast is preferably high as possible. The zinc content relative to dry mass of fungus body in a precipitate fraction obtained through washing the pulverized yeast with, for example, water is preferably 70% by mass or more, more preferably 80% by mass or more, particularly preferably 90% by mass or more, relative to the zinc content, relative to dry mass of fungus body in an unpulverized fungus body.

Note that, a method for pulverizing yeast is not particularly limited and may be appropriately selected depending on the intended purpose. For example, a physical pulverization treatment or a chemical pulverization treatment may be used. Specifically, suitable is a method using DINOMILL in which 0.5 mm-diameter beads are packed to 50% by volume.

A form of the zinc-containing yeast is not particularly limited and may be appropriately selected depending on the intended purpose. For example, the zinc-containing yeast may be in the form of a wet fungus body or powder.

The yeast may further contain other mineral components other than zinc. The mineral components are not particularly limited and may be appropriately selected depending on the intended purpose. Examples thereof include iron, copper, magnesium, and manganese. These mineral components may be contained alone or in combination in the yeast. These mineral components are, in general, preferably contained in a high concentration, but the concentration varies depending on the intended purpose and cannot be unambiguously defined.

The yeast is particularly preferably edible yeast in the case where extract thereof is used as a food material.

The edible yeast is not particularly limited and may be appropriately selected depending on the intended purpose. Examples thereof include baker's yeast, brewer's yeast, wine yeast, sake yeast, and miso and soy sauce yeast. Among them, the baker's yeast is particularly preferable.

A class of the edible yeast is not particularly limited and may be appropriately selected depending on the intended purpose. Examples thereof include the genus *Saccharomyces*, the genus *Torulopsis*, the genus *Mycotorula*, the genus *Torulaspora*, the genus *Candida*, the genus *Rhodotorula*, and the genus *Pichia*.

Specific examples of the edible yeast include *Saccharomyces cerevisiae*, *Saccharomyces carlsbergensis*, *Saccharomyces uvarum*, *Saccharomyces rouxii*, *Torulopsis utilis*, *Torulopsis candida*, *Mycotorula japonica*, *Mycotorula lipolytica*, *Torulaspora delbrueckii*, *Torulaspora fermentati*, *Candida sake*, *Candida tropicalis*, *Candida utilis*, *Hansenula anomala*, *Hansenula suaveolens*, *Saccharomycopsis fibligera*, *Saccharomyces lipolytica*, *Rhodotorula rubra*, and *Pichia farinosa*.

Among them, preferable are *Saccharomyces cerevisiae*, and *Saccharomyces carlsbergensis*, particularly preferable is *Saccharomyces cerevisiae*.

<<Carboxylic Acid and Carboxylic Acid Salt>>

The carboxylic acid is not particularly limited and may be appropriately selected depending on the intended purpose. The carboxylic acid may be a monovalent carboxylic acid or a bivalent or higher carboxylic acid. However, preferable is the bivalent or higher carboxylic acid, and more preferable is a trivalent or higher carboxylic acid, from the viewpoint of extraction efficiency of zinc.

Examples of the monovalent carboxylic acid include formic acid, acetic acid, propionic acid, butyric acid, valeric acid, caproic acid, enanthic acid, caprylic acid, pyruvic acid, and gluconic acid.

Examples of the bivalent carboxylic acid include oxalic acid, malonic acid, succinic acid, glutaric acid, adipic acid, fumaric acid, maleic acid, tartaric acid, oxaloacetic acid, and α-ketoglutaric acid.

Examples of the trivalent carboxylic acid include citric acid, isocitric acid, aconitic acid, and oxalosuccinic acid.

Among them, preferable are citric acid, succinic acid, and tartaric acid, more preferable is citric acid.

These may be used alone or in combination.

The carboxylic acid salt is not particularly limited and may be appropriately selected depending on the intended purpose. The carboxylic acid salt may be a monovalent carboxylic acid salt or a bivalent or higher carboxylic acid salt. However, preferable is the bivalent or higher carboxylic acid salt, more preferable is a trivalent or higher carboxylic acid salt, from the viewpoint of extraction efficiency of zinc. Examples of the carboxylic acid salt include salts of the above-described specific carboxylic acids. Among them, preferable are a citric acid salt, a succinic acid salt, and a tartaric acid salt, more preferable is the citric acid salt.

These may be used alone or in combination.

A type of the salt is not particularly limited and may be appropriately selected depending on the intended purpose. Examples thereof include alkali metal salts such as a sodium salt and a potassium salt; and alkali earth metal salts such as a magnesium salt and a calcium salt. These may be used alone or in combination.

Either of the carboxylic acid or the carboxylic acid salt may be used. Alternatively, both of the carboxylic acid and the carboxylic acid salt may be used.

An amount of the carboxylic acid or the carboxylic acid salt is not particularly limited and may be appropriately selected depending on the intended purpose. However, the total amount of the carboxylic acid and the carboxylic acid salt is preferably 0.2 mol or more, more preferably 1.0 mol or more, relative to 1 mol of zinc contained in the yeast. When the total amount is less than 0.2 mol, a zinc-elution rate may be deteriorated.

A solvent used for a solution containing the carboxylic acid, the carboxylic acid salt, or both thereof (hereinafter may be referred to as "carboxylic acid buffer solution") is not particularly limited and may be appropriately selected depending on the intended purpose. The solvent is typically water, and may be a mixed solution of water and an organic solvent (e.g., alcohol).

A concentration of the carboxylic acid buffer solution is not particularly limited and may be appropriately selected depending on the intended purpose. The concentration is preferably high as possible from the viewpoint of the extraction efficiency of zinc. Specifically, the concentration is preferably 20 mmol/L or more, more preferably 50 mmol/L or more, further preferably 150 mmol/L.

The pH of the carboxylic acid buffer solution is not particularly limited and may be appropriately selected depending on the intended purpose. Note that, the pH can be adjusted by varying a quantity ratio of the carboxylic acid and the carboxylic acid salt.

The pH of the suspension liquid in the extraction step is not particularly limited and may be appropriately selected depending on the intended purpose, but is preferably 3.0 to 10.0.

An extraction time and a temperature of the suspension liquid in the extraction step are not particularly limited and may be appropriately selected depending on the intended purpose.

The zinc-elution rate (hereinafter may be referred to as "extraction rate") in the extraction step is not particularly limited and may be appropriately selected depending on the intended purpose, but is preferably high as possible. Specifically, the zinc-elution rate is preferably 9% or more, more preferably 30% or more, particularly preferably 60% or more.

The zinc-elution rate can be calculated according to the following equation.

$$\text{Zinc-elution rate}(\%) = \{\text{Total amount (mass) of zinc in extract/Total amount (mass) of zinc contained in yeast used for extraction}\} \times 100$$

<<Suspension>>

A method for suspending the yeast into the solution containing the carboxylic acid, the carboxylic acid salt, or both thereof (carboxylic acid buffer solution) is not particularly limited and may be appropriately selected depending on the intended purpose. For example, known agitating methods or known shaking methods may be used.

In the extraction step, the suspension liquid may be further shaken. A shaking condition is not particularly limited and may be appropriately selected depending on the intended purpose.

<<Separation of Solid Component and Liquid Component>>

A method for separating the solid component and the liquid component in the suspension liquid is not particularly limited and may be appropriately selected depending on the intended purpose. Examples thereof include filtration or centrifugation.

A method for filtration is not particularly limited. Known filtration devices may be appropriately selected and used. Examples the filtration devices include a filter press and a line filter. Note that, these may be used in combination.

A method for centrifugation is not particularly limited. Known centrifugation devices may be appropriately selected and used. A centrifugation condition is not particularly limited and may be appropriately selected depending on an amount of the suspension liquid. For example, in the case where the amount of the suspension liquid is 5 mL, the centrifugation is performed at 3,000 rpm for 5 min.

After extraction with the carboxylic acid buffer solution, the carboxylic acid remains in the high-zinc-content yeast extract as extraction traces. Therefore, the carboxylic acid contained in the high-zinc-content yeast extract can be analyzed to determine whether the extraction with the carboxylic acid buffer solution has been performed. A method for analyzing is not particularly limited. For example, an amount of the carboxylic acid (e.g., citric acid) can be measured by means of HPLC (high performance liquid chromatography).

<Other Steps>

The other steps are not particularly limited and may be appropriately selected depending on the intended purpose, as long as they do not impair the effects of the present invention. Examples thereof include a hot-water treatment step, a drying step, a concentration step, and a dilution step. Among them, the hot-water treatment step is preferably included.

<<Hot-Water Treatment Step>>

The hot-water treatment step is a step of suspending the yeast containing zinc into hot-water of 60° C. to 120° C. to thereby obtain a suspension liquid, and separating a solid component and a liquid component of the suspension liquid, prior to the extraction step. Performing the hot-water treatment step prior to the extraction step is preferable, because the odor and the taste which are distinctive of yeast (i.e., yeast odor and yeast taste) can be reduced, and a taste of food to which the resultant high-zinc-content yeast extract has been added is not impaired.

A temperature of the hot-water is not particularly limited and may be appropriately selected depending on the intended purpose. The higher the temperature is, the higher an effect of reducing the yeast odor and the yeast taste is. The temperature is more preferably 80° C. to 120° C., further preferably 95° C. to 120° C.

Note that, a method for suspending the yeast and a method for separating the solid component and the liquid component of the suspension liquid are not particularly limited. For example, the methods described for the extraction step may be used.

In the hot-water treatment step, an extraction accelerator for accelerating extraction (removal) of the yeast odor and the yeast taste is preferably added in order to reduce the odor and taste which are distinctive of yeast. The extraction accelerator is not particularly limited and may be appropriately selected depending on the intended purpose, as long as it does not adversely affect the zinc-elution rate in the subsequent extraction step. Phosphoric acid salts are preferably added because they are superior in extraction of the yeast odor, but are less likely to accelerate extraction of zinc. An amount of the extraction accelerator to be added is not particularly limited and may be appropriately selected depending on the intended purpose, but is preferably 5% by mass to 50% by mass, more preferably 20% by mass to 50% by mass, relative to dry mass of fungus body of the yeast.

<<Drying Step, Concentration Step, Dilution Step>>

The drying step is a step of drying the high-zinc-content yeast extract.

A method for drying is not particularly limited and may be appropriately selected depending on the intended purpose. For example, SPRAY DRIER L-8 (manufactured by OHKAWARA KAKOHKI CO., LTD.) may be used. The drying step can result in a solid high-zinc-content yeast extract (powdered high-zinc-content yeast extract), which can be used in various applications described below. Note that, during the high-zinc-content yeast extract is formed into the solid high-zinc-content yeast extract, an excipient (e.g., dextrin) may be appropriately added.

The concentration step is a step of concentrating the high-zinc-content yeast extract. The dilution step is a step of diluting the high-zinc-content yeast extract.

A method for concentrating and a method for diluting are not particularly limited and may be conventionally known methods.

(High-Zinc-Content Yeast Extract)

A high-zinc-content yeast extract of the present invention is a high-zinc-content yeast extract which contains 0.4% by mass or more of zinc derived from a fungus body of yeast, and which has a turbidity of 0.10 or less in terms of absorbance at a wavelength of 660 nm (O. D. 660) when 1 g of the high-zinc-content yeast extract is dissolved or dispersed into 100 mL of water.

A method for producing the high-zinc-content yeast extract is not particularly limited and may be appropriately selected depending on the intended purpose. However, the high-zinc-content yeast extract can be suitably produced by the method for producing the high-zinc-content yeast extract of the present invention. That is, the high-zinc-content yeast extract is preferably produced by subjecting the zinc-containing yeast to extraction with a solution containing a carboxylic acid, a carboxylic acid salt, or both thereof.

<Zinc-Content>

The zinc-content in the high-zinc-content yeast extract is preferably high as possible from the viewpoint of use of the high-zinc-content yeast extract as a zinc-enriched food material. "High-zinc-content," as used herein, means that zinc is contained in a concentration of 0.4% by mass or more, preferably 3% by mass or more, more preferably 5% by mass or more.

Containing zinc in such a high concentration allows the high-zinc-content yeast extract to be suitably used as an oral or tube feeding composition (e.g., a liquid food or a beverage) and a food material.

Note that, the zinc-content can be measured by known methods such as an atomic absorption spectrometry or an ICP emission spectrometric analysis.

<Turbidity>

The high-zinc-content yeast extract of the present invention has a high water-solubility, so that an aqueous solution of the high-zinc-content yeast extract has a high transparency. The high-zinc-content yeast extract has a turbidity of 0.10 or less, preferably 0.05 or less, more preferably 0.01 or less in terms of absorbance at a wavelength of 660 nm (O. D. 660) when 1 g of the high-zinc-content yeast extract is dissolved or dispersed into 100 mL of water. When the turbidity is more than 0.10, food to which the high-zinc-content yeast extract is added may get turbid and be discolored, which may impair appearance of the food. In addition, the high-zinc-content yeast extract has insufficient water-solubility and may precipitate, which may be problematic in the case where the high-zinc-content yeast extract is used in food required to be transparent (in particular, soft drink).

A form of the high-zinc-content yeast extract is not particularly limited and may be appropriately selected depending on the intended purpose. Examples thereof include a liquid (extraction liquid such as filtrate or supernatant) form obtained through the extraction step; a solid form such as a powdered (powder) form, a particle form, or a sheet form; and a semi-solid form such as a gel form or a slurry form. In the measurement of the turbidity, "1 g of the high-zinc-content yeast extract" is in the form of a dried solid of which moisture content is 7% by mass or less. A method for drying is not particularly limited and may be the above-described methods. A drying condition is not particularly limited.

Note that, the turbidity can be measured as absorbance at a wavelength of 660 nm (O. D. 660) by means of a spectrophotometer. Example of the spectrophotometer includes U-2000 (manufactured by Hitachi, Ltd.).

<Application>

Application of a high-zinc-content yeast extract of the present invention is not particularly limited and may be appropriately selected depending on the intended purpose. The high-zinc-content yeast extract is preferably used as a food material to be added to food, animal food, or feed, particularly preferably as the food material. Among the food materials, the high-zinc-content yeast extract of the present invention is preferably used in the liquid food or the soft drink from the viewpoint of excellent solubility. In addition, the high-zinc-content yeast extract is also preferably used in a food fermentation medium or as an agent for maintaining and restoring a green color of vegetables. The high-zinc-content yeast extract of the present invention can result in high-zinc-content food, high-zinc-content animal food, and high-zinc-content feed.

A form of the high-zinc-content yeast extract in use is not particularly limited and may be appropriately selected depending on the intended application. Examples thereof include a dried powder form (e.g., extract dried by means of, for example, a spray drier), a solution form in which the high-zinc-content yeast extract is dissolved in a solvent, and a semi-solid form (e.g., a gel form or cream form). Note that, a method for forming the high-zinc-content yeast extract into the above-described forms is not particularly limited and can be performed by means of known devices according to known methods.

(Food)

Food of the present invention contains a high-zinc-content yeast extract of the present invention; and, if necessary, further contains other ingredients.

The "food," as used herein, refers to those having a low possibility of being harmful to human health, and being ingested via oral or gastrointestinal administration in an ordinary social life, which is not limited by administrative classification such as food, medicine, or quasi drug. For example, the food encompasses a wide range of orally ingested general food, health food, food with health claims, quasi drug and medicine.

A type of the food is not particularly limited and may be appropriately selected depending on the intended purpose, but is preferably a liquid food, bread, confectionery such as a biscuit or a cracker, a processed marine product, a processed meat product, noodles, a seasoning such as miso, a processed vegetable product, a beverage such as juice, ices such as ice cream, and health food, particularly preferably the liquid food or the beverage.

An amount of the high-zinc-content yeast extract contained in the food is not particularly limited and may be appropriately selected depending on the intended application and purpose.

The other ingredients are not particularly limited and may be appropriately selected depending on the intended purpose. Examples thereof include auxiliary materials or additives generally used in production of the food.

The auxiliary materials or additives are not particularly limited and may be appropriately selected depending on the intended purpose. Examples thereof include glucose, fructose, sucrose, maltose, sorbitol, stevioside, rubusoside, corn syrup, lactose, citric acid, tartaric acid, malic acid, succinic acid, lactic acid, L-ascorbic acid, dl-α-tocopherol, sodium erythorbate, glycerin, propylene glycol, glycerine fatty acid ester, polyglycerin fatty acid ester, sucrose fatty acid ester, sorbitan fatty acid ester, gum arabic, carrageenan, casein, gelatin, pectin, agar, vitamin B, nicotinic acid amide, calcium pantothenate, amino acids, calcium salts, a pigment, a perfume, and a preservative.

An amount of the other ingredients is not particularly limited and may be appropriately selected depending on the intended purpose.

(Agent for Maintaining and Restoring Green Color of Vegetables)

An agent for maintaining and restoring a green color of vegetables of the present invention contains a high-zinc-content yeast extract of the present invention; and, if necessary, further contains other ingredients.

Intended vegetables of the agent for maintaining and restoring a green color are not particularly limited and may be appropriately selected depending on the intended purpose, as long as they are edible green plants. For example, the agent for maintaining and restoring a green color can maintain and restore a green color of salt-pickled green plants and commercially available pickled vegetables. Specific examples include a salted bracken, a salted nozawana (*Brassica rapa* L. var. *hakabura*), a salted cucumber, or a green pepper.

An amount of the high-zinc-content yeast extract contained in the agent for maintaining and restoring a green color of vegetables is not particularly limited and may be appropriately selected depending on the intended application and purpose.

The other ingredients are not particularly limited and may be appropriately selected depending on the intended purpose. Examples thereof include the above-described auxiliary materials or additives.

EXAMPLES

Examples of the present invention now will be described, but the present invention is not limited thereto.

Example 1 and Comparative Example 1

Elution of Zinc with Carboxylic Acid Salt

To 5 g (dry mass) of a high-zinc-content yeast powder (MINERAL YEAST ZN5, zinc-content: 54,400 ppm by mass, manufactured by Oriental Yeast Co., Ltd.), was added 50 mL of each of aqueous solutions of carboxylic acid sodium salts described in Table 1 at 200 mmol/L, followed by stirring and diluting to 100 mL with water to thereby obtain a suspension liquid. Note that, an amount of each of the carboxylic acid salts was 2.4 mol relative to 1 mol of zinc contained in yeast to be subjected to extraction. Water or a 200 mmol/L aqueous solution of sodium chloride (table salt) was used as a control and was tested in the same manner as the suspension liquid. The suspension liquid was measured for pH by means of a pH meter (MP230, manufactured by Mettler-Toledo International Inc.).

Under stirring with a stirrer, 5 mL of the suspension liquid was taken out into a test tube, followed by heating in a boiling water bath for 10 min. The resultant suspension liquid is centrifuged at 3,000 rpm for 5 min. Only the resultant supernatant (extraction liquid) was transferred to a test tube to thereby obtain yeast extract. The yeast extract was weighed.

The zinc-content was determined by measuring the zinc-content in the yeast extract through an ICP emission spectrometric analysis by means of an ICP emission spectrophotometer (OPTIMA 2100DV, manufactured by PerkinElmer Inc.), from which a rate of zinc eluted to the extraction liquid was calculated. Results are shown in Table 1 and FIG. 1.

The zinc-content in the extract on a dry powder basis (% by mass) was measured as follows. That is, dextrin was added to the extraction liquid which had been subjected to extraction, followed by adjusting a solid content to 12% by mass. Then, the resultant was dried by means of SPRAY DRIER L-8 (manufactured by OHKAWARA KAKOHKI CO., LTD.), and quantified for zinc by the ICP emission spectrometric analysis by means of the ICP emission spectrophotometer (OPTIMA 2100DV, manufactured by PerkinElmer Inc.). Results are shown in Table 1.

TABLE 1

| | Type of extraction solvent | pH of suspension liquid | Zinc-elution rate (%) | Zinc-content on dry powder basis (% by mass) |
|---|---|---|---|---|
| Comp. Ex. 1-1 | Pure water | 7.5 | 6 | 0.2 |
| Comp. Ex. 1-2 | Sodium chloride (table salt) aqueous solution | 7.5 | 8 | 0.3 |
| Ex. 1-1 | Sodium acetate aqueous solution | 7.6 | 9 | 0.4 |
| Ex. 1-2 | Sodium gluconate aqueous solution | 7.8 | 15 | 0.6 |
| Ex. 1-3 | Monosodium Succinate aqueous solution | 5.3 | 54 | 2.0 |
| Ex. 1-4 | L-sodium tartrate aqueous solution | 7.9 | 34 | 1.3 |
| Ex. 1-5 | Trisodium citrate aqueous solution | 9.4 | 85 | 3.2 |

As can be seen from Table 1 and FIG. 1, use of carboxylic acid salts result in a high zinc-elution rate and a high-zinc-content extract. This effect was the highest in the citrate, which was a trivalent carboxylic acid, followed by the succinate and the tartrate, which were bivalent carboxylic acids. The pHs of the suspension liquids were in neutral to alkaline, with the exception of succinate. Therefore, zinc is thought to be eluted due to the chelate effect. Note that, although the succinate and the tartrate are both bivalent carboxylic acid salts, the elution rate of the succinate is higher than that of the tartrate, which is thought to be resulted from a difference of pH.

Example 2

Effect of pH on Zinc-Elution Rate

MINERAL YEAST ZN5 powder (manufactured by Oriental Yeast Co., Ltd.) was suspended into 300 mL of water to thereby obtain 40% by mass of cream. The resultant cream was heated for 10 min in a boiling water bath, followed by washing. The resultant precipitate was diluted to 300 mL with water. Then, 10 mL of the resultant cream was added to and suspended into 10 mL of each of aqueous solutions containing citric acid, trisodium citrate, or both thereof (citric acid buffer solutions) described in the following Table 2, to thereby obtain a suspension liquid. Note that, all of the citric acid buffer solutions had a concentration of 200 mmol/L, and the pH of each of the citric acid buffer solutions was adjusted by appropriately varying a quantity ratio of citric acid and trisodium citrate.

Two hours after suspending each of the citric acid buffer solutions, the resultant suspension liquid was subjected to centrifugation. The resultant supernatant (yeast extract) was measured for the zinc-elution rate in the same manner as in Example 1. Additionally, the yeast extract was dried to thereby obtain dry powder, which was measured for the zinc-content in the same manner as in Example 1. Results are shown in the following Table 2 and FIG. 2.

TABLE 2

| | pH of aqueous solution containing citric acid, trisodium citrate, or both thereof (citric acid buffer solution) | pH of suspension liquid | Zinc-elution rate (%) | Zinc-content on dry powder basis (% by mass) |
|---|---|---|---|---|
| Ex. 2-1 | 1.9 (only citric acid) | 3.0 | 94 | 5.5 |
| Ex. 2-2 | 3.0 | 3.6 | 91 | 5.3 |
| Ex. 2-3 | 3.5 | 4.1 | 86 | 4.9 |
| Ex. 2-4 | 4.0 | 4.6 | 93 | 5.4 |
| Ex. 2-5 | 4.5 | 5.3 | 92 | 5.3 |
| Ex. 2-6 | 5.0 | 6.4 | 85 | 4.9 |
| Ex. 2-7 | 5.5 | 7.3 | 87 | 5.0 |
| Ex. 2-8 | 6.0 | 8.5 | 78 | 4.5 |
| Ex. 2-9 | 6.5 | 9.4 | 74 | 4.3 |
| Ex. 2-10 | 7.0 | 9.6 | 71 | 4.1 |
| Ex. 2-11 | 7.5 | 9.7 | 74 | 4.3 |
| Ex. 2-12 | 8.2 (only trisodium citrate) | 9.7 | 80 | 4.7 |

Figure 2:
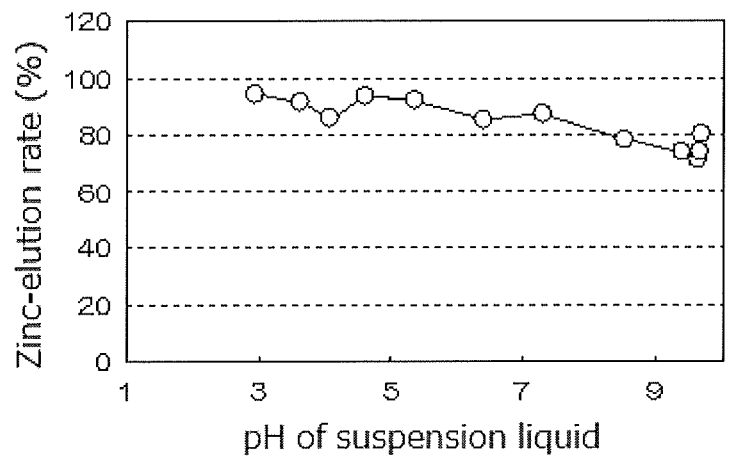
FIG. 2 is a graph illustrating an effect of pH of a suspension liquid on a zinc-elution rate in Example 2.

As can be seen from Table 2 and FIG. 2, there is a trend that the lower the pH of a solvent used for extraction (carboxylic acid buffer solution) is, the higher the zinc-elution rate (elution rate) is. However, when the suspension liquid had the pH of 3 to 10, it had a high zinc-elution rate of 70% or more, that is, the high-zinc-content yeast extract could be obtained.

Example 3 and Comparative Example 2

Effect of Total Amount of Carboxylic Acid and Carboxylic Acid Salt on Zinc-Content in Yeast and Zinc Elution Rate MINERAL YEAST ZN5 (manufactured by Oriental Yeast Co., Ltd.) was used as a raw material to test a relationship between the concentration of a carboxylic acid buffer solution and the extraction efficiency of zinc. Citric acid was used as a carboxylic acid contained in an extraction solvent to prepare citric acid buffer solutions having concentrations described in the following Table 3. The pH of each of the citric acid buffer solutions was adjusted to 5.0 by appropriately varying a quantity ratio of citric acid and trisodium citrate.

The yeast extracts were obtained in the same manner as in Example 2, except that the concentration of the cream of MINERAL YEAST ZN5, which is a raw material, was changed to 37.7% by mass, and citric acid buffer solutions having concentrations described in the following Table 3 were used. The resultant yeast extracts were measured for the zinc-elution rate. Additionally, each of the extracts was dried to thereby obtain dry powder, which was measured for the zinc-content in the same manner as in Example 1. Results are shown in the following Table 3 and FIG. 3.

TABLE 3

| | Concentration of citric acid buffer solution (pH 5.0) (mmol/L) | Molar ratio (carboxylic acid and carboxylic acid salt/zinc) | Zinc-elution rate (%) | Zinc-content on dry powder basis (% by mass) |
|---|---|---|---|---|
| Comp. Ex. 2 | 0 | — | 3 | 0.2 |
| Ex. 3-1 | 25 | 0.2 | 32 | 1.9 |
| Ex. 3-2 | 50 | 0.4 | 53 | 3.2 |
| Ex. 3-3 | 75 | 0.6 | 72 | 4.2 |
| Ex. 3-4 | 100 | 0.8 | 79 | 4.7 |
| Ex. 3-5 | 125 | 1.0 | 84 | 5.0 |
| Ex. 3-6 | 150 | 1.2 | 87 | 5.2 |
| Ex. 3-7 | 175 | 1.4 | 96 | 5.7 |
| Ex. 3-8 | 200 | 1.7 | 97 | 5.8 |
| Ex. 3-9 | 300 | 2.5 | 90 | 5.6 |
| Ex. 3-10 | 400 | 3.3 | 94 | 5.6 |
| Ex. 3-11 | 500 | 4.1 | 96 | 5.7 |

Figure 3:
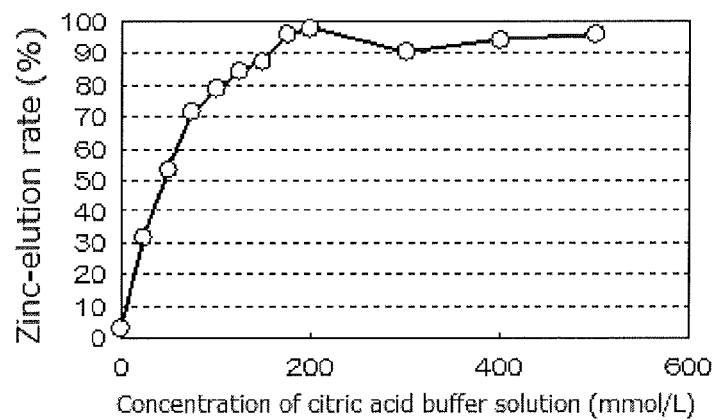
FIG. 3 is a graph illustrating a relationship between a concentration of a carboxylic acid buffer solution and a zinc-elution rate in Example 3 and Comparative Example 2.

As can be seen from Table 3 and FIG. 3, the zinc-elution rate depends on the molar ratio of zinc to a carboxylic acid and salt thereof. When the total amount of the carboxylic acid and the carboxylic acid salt is 0.2 mol to 5.0 mol relative to 1 mol of zinc in yeast to be extracted, the zinc-elution rate is high, and the zinc-content of extract (dry powder) is also high.

Test Example 1

Effect of Extraction Accelerator for Removing Yeast Odor and Ultraviolet Absorbing Material Upon pretreatment with hot-water, aqueous solutions of extraction accelerators described in Table 4 were added to determine an effect of removing a yeast odor and an ultraviolet absorbing material.

Firstly, 5 g of MINERAL YEAST ZN5 powder (manufactured by Oriental Yeast Co., Ltd.) was suspended into 50 mL of each of the aqueous solutions. The resultant suspension liquid was measured for the pH, and diluted to 100 mL with water to thereby obtain a yeast suspension liquid. Here, a final concentration of chitosan was adjusted to 0.5% (28 mmol/L assuming that a molecular weight of glucosamine is 179), and a final concentration of each of extraction accelerators other than chitosan was adjusted to 100 mmol/L. The suspension liquid was dispensed in 5 mL aliquots, each of which was immersed in a boiling water bath for 10 min and then centrifuged. The resultant supernatant was filtered through a filter for ICP. The resultant filtrate (yeast extract) was measured for absorbances at wavelengths of 260 nm and 280 nm (A260 and A280), evaluated for the yeast odor, and measured for the zinc-elution rate. Results are shown in Table 4 and FIG. 4.

The A260 and A280 were measured by means of a spectrophotometer (U-2000, manufactured by Hitachi, Ltd.).

The yeast odor was evaluated in the following 5 grades by relatively evaluating yeast odors of test examples through sensory evaluation: grade 1: very weak, grade 2: weak, grade 3: perceptible, grade 4: strong, and grade 5: very strong.

The zinc rate was determined as follows. The zinc-content in the yeast extract was measured through the ICP emission spectrometric analysis by means of the ICP emission spectrophotometer (OPTIMA 2100DV, manufactured by PerkinElmer Inc.). Thereafter, the zinc rate eluted to the extraction liquid was calculated assuming that the zinc-content in the total amount of the suspension liquid was 14,400 ppm (=5 g×5.75%×5 mL), and that the amount of the extraction liquid extracted with each of the extraction accelerators was 4.3 mL.

Figure 4:
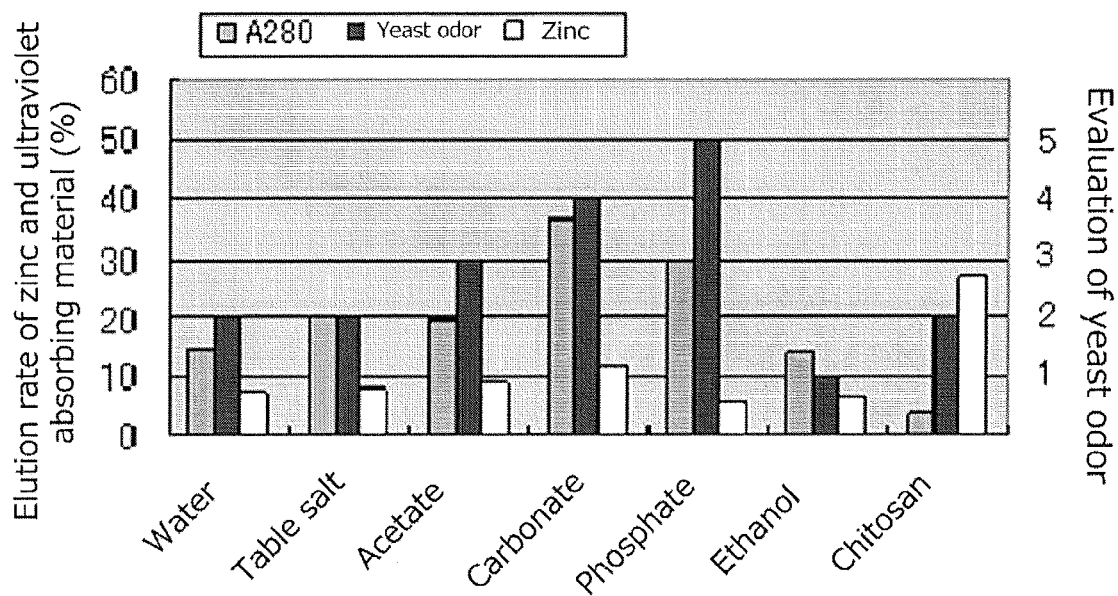
FIG. 4 is a graph illustrating effects of extraction accelerators for removing a yeast odor and an ultraviolet absorbing material, and zinc-elution rates in Test Example 1.

As can be seen from Table 4 and FIG. 4, among tested extraction accelerators, sodium hydrogenphosphate, which is phosphate, is the most excellent because it is excellent in extraction of the yeast odor and the ultraviolet absorbing material, and results in a low zinc-elution rate. Therefore, phosphoric acid treatment before the extraction step of the yeast extract with the carboxylic acid buffer solution can result in a high-zinc-content yeast extract in which the yeast odor and the ultraviolet absorbing material are reduced.

Example 4 and Comparative Example 3

Evaluation of Solubility

One gram of the high-zinc content yeast extract powder obtained in Example 3-8 was dissolved in 100 mL of water to thereby produce a 1% (w/v) aqueous solution of the high-zinc content yeast extract. The aqueous solution was measured for turbidity by measuring absorbance at a wavelength of 660 nm (O. D. 660) by means of the spectrophotometer (U-2000, manufactured by Hitachi, Ltd.). The aqueous solution was observed for the presence or absence of a precipitate after centrifugation at 3,000 rpm for 5 min.

Figure 5A:
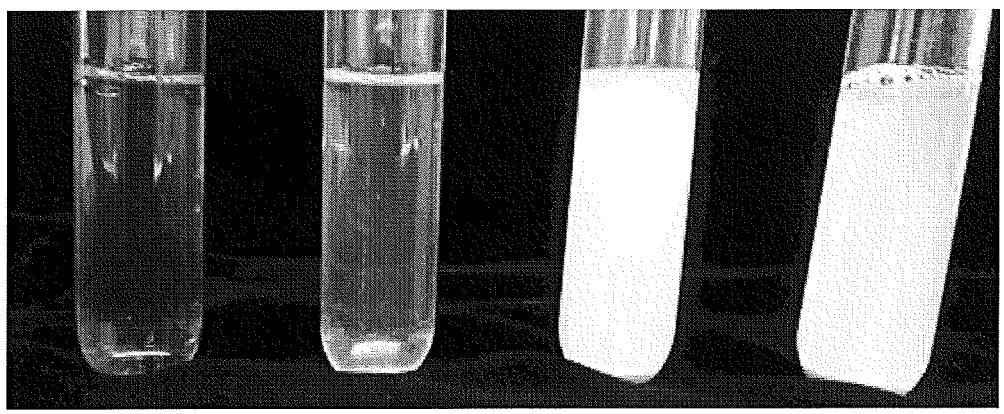
FIG. 5A is one exemplary photograph illustrating water-solubilities of high-zinc-content yeast extracts in Example 4 and Comparative Example 3.
Figure 5B:
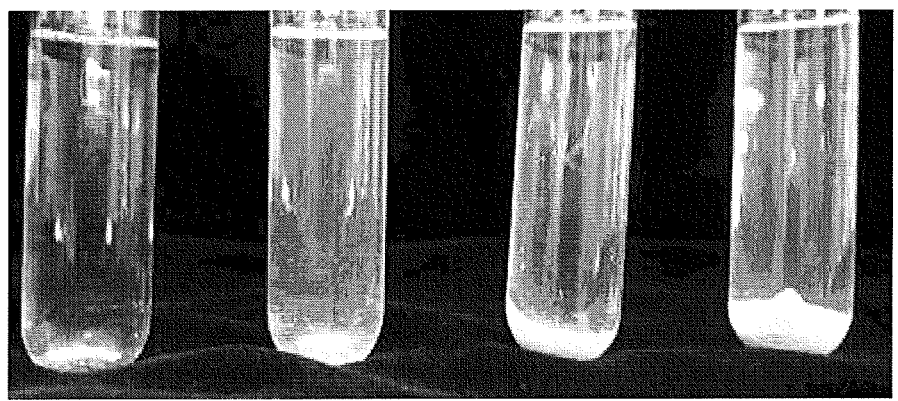
FIG. 5B is a photograph of aqueous solutions in FIG. 5A after centrifugation at 3,000 rpm for 5 min.

As a control, a high-zinc-content yeast extract (SOLUBLE ZINC YEAST, manufactured by Grow Company, Inc.), which is a conventional product, unextracted MINERAL YEAST ZN5 (manufactured by Oriental Yeast Co., Ltd.), and MINERAL YEAST ZN5-F (manufactured by Oriental Yeast Co., Ltd.) were measured for turbidity and evaluated for the presence or absence of a precipitate in the same manner. Results are Table 5 and FIGS. 5A and 5B.

TABLE 4

|  | Type of extraction accelerator | pH of suspension liquid | A260 | A280 | Yeast odor | Zinc rate eluted with extraction accelerator (%) |
| --- | --- | --- | --- | --- | --- | --- |
| Test Example 1-1 | Water | 5.7 | 32.4 | 14.2 | 2 | 7 |
| Test Example 1-2 | Sodium chloride (table salt) | 7.5 | 44.6 | 19.9 | 2 | 8 |
| Test Example 1-3 | Sodium acetate | 7.6 | 53.8 | 19.4 | 3 | 9 |
| Test Example 1-4 | Sodium bicarbonate | 8.0 | 76.6 | 36.6 | 4 | 12 |
| Test Example 1-5 | Sodium hydrogenphosphate | 5.9 | 63.6 | 29.8 | 5 | 5 |
| Test Example 1-6 | Ethanol | 7.6 | 32.4 | 14 | 1 | 6 |
| Test Example 1-7 | Chitosan | 5.6 | 9.8 | 4.2 | 2 | 27 |

TABLE 5

| | Sample | O.D. 660 (1% aqueous solution) | Visual evaluation | Visual evaluation after centrifugation |
|---|---|---|---|---|
| Ex. 4 | High-zinc-content yeast extract | 0.004 | Aqueous solution with high clarity | Precipitate was not confirmed |
| Comp. Ex. 3-1 | Conventional product | 0.139 | Aqueous solution with slight turbidity | Precipitate was confirmed |
| Comp. Ex. 3-2 | MINERAL YEAST ZN5 | 15.6 | Suspended aqueous solution | Precipitate was confirmed |
| Comp. Ex. 3-3 | MINERAL YEAST ZN5-F | 5.6 | Suspended aqueous solution | Precipitate was confirmed |

The aqueous solution of Example 4 had significantly lower turbidity than the aqueous solution of Comparative Example 3-1. As can be seen from FIG. 5A, it was visually confirmed that the aqueous solution of Example 4 had significantly higher clarity than the aqueous solution of Comparative Example 3-1. As can be seen from FIG. 5B, after centrifugation at 3,000 rpm for 5 min, the aqueous solution of Example 4 contained no precipitate and was a solution with high clarity. In contrast, the aqueous solution of Comparative Example 3-1 contained a precipitate.

Therefore, the high-zinc-content yeast extract of the present invention has higher solubility than the conventional product, so that it can be added to the liquid food or the beverage. Additionally, the high-zinc-content yeast extract of the present invention does not cause turbidity and discoloration, so that it can be added to, in particular, a soft drink having a high transparency.

Each sample was ranked for evaluation items by 6 evaluators according to the following criteria, assuming that the high-zinc-content yeast extract was ranked as 3 for each of evaluation items, followed by averaging. Note that, as a control, the conventional product (SOLUBLE ZINC YEAST, manufactured by Grow Company, Inc.), unextracted high-zinc-content yeast (MINERAL YEAST ZN5 and MINERAL YEAST ZN5-F, both manufactured by Oriental Yeast Co., Ltd.) were evaluated in the same manner. Results are shown in Table 6.

—Evaluation Criteria—
5: very strong
4: strong
3: comparable
2: weak
1: very weak

TABLE 6

| | | Powder | | 1% Aqueous solution (w/v) | | Milk | | Liquid food | |
|---|---|---|---|---|---|---|---|---|---|
| | Sample | Yeast odor | Extract odor | Yeast odor | Extract odor | Strength of odor | Strength of taste | Strength of odor | Strength of taste |
| Ex. 5 | High-zinc-content yeast extract | 3 | 3 | 3 | 3 | 3 | 3 | 3 | 3 |
| Comp. Ex. 4-1 | Conventional product | 3 | 5 | 4 | 5 | 5 | 4 | 4 | 4 |
| Comp. Ex. 4-2 | MINERAL YEAST ZN5 | 5 | 4 | 5 | 4 | 4 | 3 | 5 | 3 |
| Comp. Ex. 4-3 | MINERAL YEAST ZN5-F | 4 | 4 | 4 | 4 | 4 | 3 | 4 | 3 |

Example 5 and Comparative Example 4

Evaluation of Odor and Taste

The high-zinc-content yeast extract powder obtained in Example 3-8, a 1% (w/v) aqueous solution of the powder, a 1% (w/w) solution of the powder in an aqueous solution produced by dissolving or suspending 14 g of modified milk powder (CHIL MIL, manufactured by MORINAGA MILK INDUSTRY CO., LTD.) into 100 mL of water (hereinafter referred to as "milk"), and a nutritional adjustment food (MEIBALANCE (yogurt taste), manufactured by Meiji Co., Ltd.) containing 1% (w/w) of the powder (hereinafter referred to as "liquid food") were prepared.

<Evaluation Method>

The above-described high-zinc-content yeast extract, 1% aqueous solution, milk, and liquid food were evaluated for the yeast odor, an extract odor, the yeast taste, and an extract taste, which were distinctive of yeast or yeast extract, by 6 evaluators.

As can be seen from Table 6, the high-zinc-content yeast extract of Example 5 was evaluated to have a significantly lower extract odor than that of Comparative Example 4-1 (conventional product) in the powder and the 1% aqueous solution; and to have significantly lower extract odor and extract taste in the milk and the liquid food. Therefore, the high-zinc-content yeast extract of the present invention was found to have reduced odor and taste which were distinctive of yeast or yeast extract, so that the high-zinc-content yeast extract does not impair a flavor of food containing it.

Example 6-1

Evaluation of Effect for Maintaining and Restoring Green Color of Salted Bracken-1

Figure 6A:
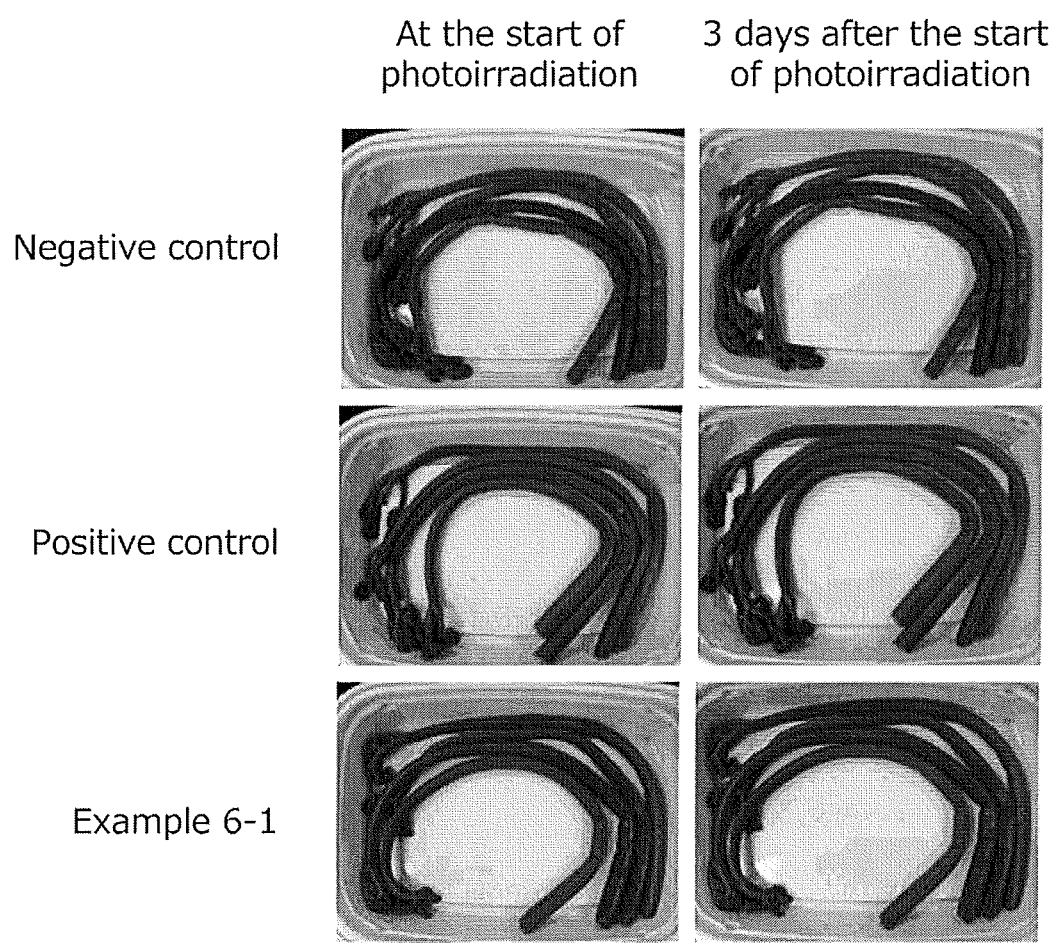
FIG. 6A is one exemplary photograph illustrating an effect for maintaining and restoring a green color of a vegetable in Example 6-1.

A 1% (w/v) aqueous solution of the high-zinc-content yeast extract powder obtained in Example 3-8 was prepared. The aqueous solution was boiled, to which a salted bracken (manufactured by Onoyashoten Limited Company) lightly washed with water was added. After reboiling, the salted bracken was boiled for 15 min, followed by draining with a colander and cooling with running water. The resultant cool salted bracken was photoirradiated at a light intensity of 600 luxes at 10° C., and observed at the start of photoirradiation and 3 days after the start of photoirradiation. FIG. 6A shows salted brackens at each time. Table 7-1 shows measurement results obtained by means of a color difference meter (CR-400, manufactured by Konica Minolta, Inc.).

Note that, as a positive control, LEVELUP VG (mineral-containing lactobacillus, manufactured by Oriental Yeast Co., Ltd., see Japanese Patent (JP-B) No. 4700497) was prepared to have the same zinc-content, followed by subjecting to the above-described test in the same manner. As a negative control, a solution containing neither the high-zinc-content yeast extract nor LEVELUP VG was subjected to the test in the same manner.

TABLE 7-1

|  | At the start of photoirradiation | | | 3 days after the start of photoirradiation | | |
| --- | --- | --- | --- | --- | --- | --- |
|  | L* | a* | b* | L* | a* | b* |
| Negative control | 43.762 | −1.652 | 16.650 | 43.994 | −1.484 | 15.870 |
| Positive control | 45.774 | −7.378 | 18.494 | 46.066 | −7.702 | 18.282 |
| Ex. 6-1 | 46.706 | −8.794 | 18.916 | 46.972 | −9.056 | 19.782 |

Note that, in the measurement by the color difference meter, the larger a value of "L*" is, the brighter the color is, and the smaller the value of "L*" is, the darker the color is. The larger a value of "a*" is, the more red the color is, and the smaller the value of "a*" is, the more green the color is. The larger a value of "b*" is, the more yellow the color is, and the smaller the value of "b*" is, the more blue the color is.

As can be seen from FIG. 6A and Table 7-1, in Example 6-1 using the high-zinc-content yeast extract of the present invention, the salted bracken had had a green color since the start of photoirradiation and had not discolored even 3 days after the start of photoirradiation, which indicates an effect approximately equivalent to LEVELUP VG serving as the positive control. Note that, in the negative control, the salted bracken had had a brown color and a high a* value since the start of photoirradiation.

Example 6-2

Evaluation of Effect for Maintaining and Restoring Green Color of Salted Bracken-2

Figure 6B:
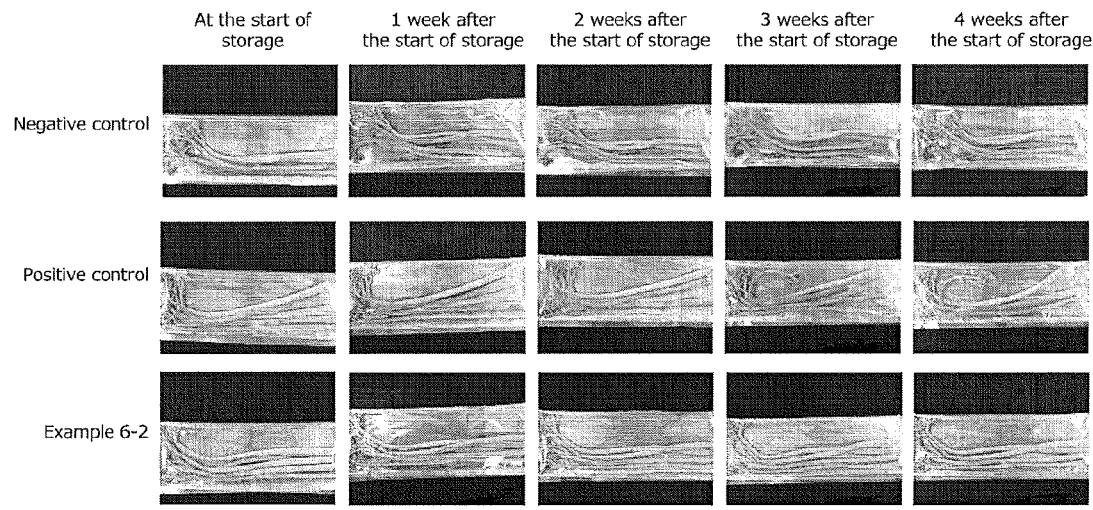
FIG. 6B is one exemplary photograph illustrating an effect for maintaining and restoring a green color of a vegetable in Example 6-2.

A 1% (w/v) aqueous solution of the high-zinc-content yeast extract powder obtained in Example 3-8 was prepared. The aqueous solution was boiled, to which a salted bracken (manufactured by Onoyashoten Limited Company) lightly washed with water was added. After reboiling, the salted bracken was boiled for 15 min, followed by draining with a colander and cooling with running water. The resultant cool salted and water were vacuum-packed together at a mass ratio of 1:1, followed by storing for 4 weeks at 5° C. FIG. 6B shows salted brackens at the start of storage, 1 week after the start of storage, 2 weeks after the start of storage, 3 weeks after the start of storage, and 4 weeks after the start of storage. Table 7-2 shows measurement results obtained by means of the color difference meter (CR-400, manufactured by Konica Minolta, Inc.) at the start of storage, 2 weeks after the start of storage, and 4 weeks after the start of storage.

Note that, as a positive control, LEVELUP VG (mineral-containing lactobacillus, manufactured by Oriental Yeast Co., Ltd., see JP-B No. 4700497) was prepared to have the same zinc-content, followed by subjecting to the test in the same manner. As a negative control, a solution containing neither the high-zinc-content yeast extract nor LEVELUP VG was subjected to the test in the same manner.

TABLE 7-2

|  | At the start of photoirradiation | | | 2 weeks after the start of storage | | | 4 weeks after the start of storage | | |
| --- | --- | --- | --- | --- | --- | --- | --- | --- | --- |
|  | L* | a* | b* | L* | a* | b* | L* | a* | b* |
| Negative control | 42.222 | −1.696 | 17.274 | 45.696 | −0.738 | 15.446 | 48.280 | −1.410 | 17.252 |
| Positive control | 46.088 | −7.022 | 19.328 | 45.630 | −7.584 | 16.818 | 47.658 | −8.738 | 18.210 |
| Ex. 6-2 | 45.686 | −8.404 | 18.138 | 47.216 | −8.306 | 17.650 | 47.862 | −7.944 | 17.704 |

As can be seen from FIG. 6B and Table 7-2, in Example 6-2 using the high-zinc-content yeast extract of the present invention, the salted bracken had had a green color since the start of photoirradiation and had not discolored even 2 weeks and 4 weeks after the start of photoirradiation, which indicates an effect approximately equivalent to LEVELUP VG serving as the positive control. Note that, in the negative control, the salted bracken had had a brown color and a high a* value since the start of photoirradiation.

Example 7-1

Evaluation of Effect for Maintaining and Restoring Green Color of Salted Nozawana-1

Figure 7A:
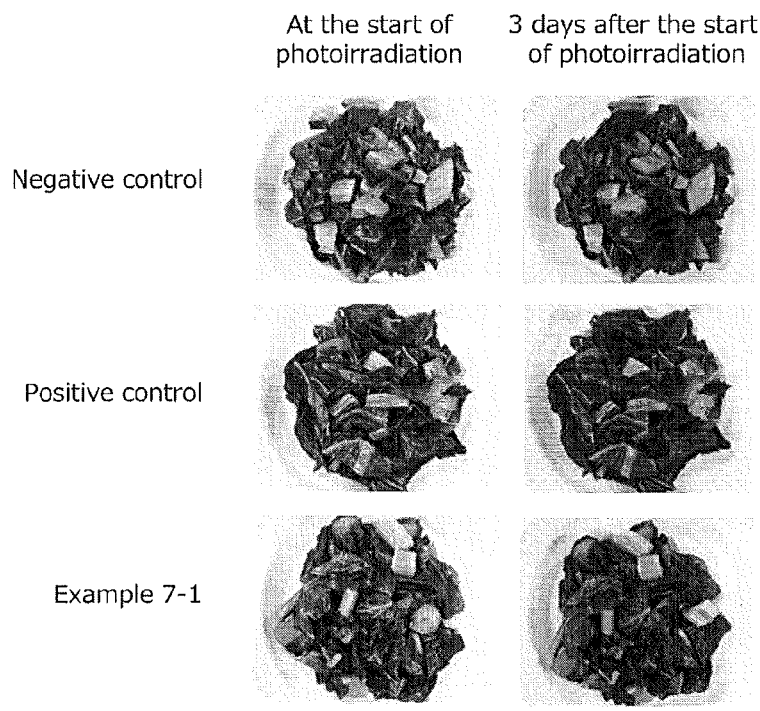
FIG. 7A is one exemplary photograph illustrating an effect for maintaining and restoring a green color of a vegetable in Example 7-1.

The photoirradiation test was performed in the same manner as in Example 6-1, except that the salted bracken was changed to a salted nozawana (manufactured by Taniguchi jozo Co., Ltd.). FIG. 7A shows salted nozawanas at the start of photoirradiation and 3 days after the start of photoirradiation. Table 8-1 shows measurement results obtained by means of a color difference meter (CR-400, manufactured by Konica Minolta, Inc.).

Note that, a positive control and a negative control were the same as in Example 6-1.

TABLE 8-1

| | At the start of photoirradiation | | | 3 days after the start of photoirradiation | | |
|---|---|---|---|---|---|---|
| | L* | a* | b* | L* | a* | b* |
| Negative control | 39.332 | −3.264 | 9.854 | 36.544 | −2.852 | 8.776 |
| Positive control | 36.188 | −5.858 | 7.412 | 37.108 | −6.292 | 8.798 |
| Ex. 7-1 | 39.278 | −6.430 | 9.558 | 35.204 | −5.488 | 6.870 |

As can be seen from FIG. 7A and Table 8-1, in Example 7-1 using the high-zinc-content yeast extract of the present invention, the salted nozawana had had a green color since the start of photoirradiation and had not discolored even 3 days after the start of photoirradiation, which indicates an effect approximately equivalent to LEVELUP VG serving as the positive control. Note that, in the negative control, the salted nozawana had had a brown color and a high a* value since the start of photoirradiation.

Example 7-2: Evaluation of Effect for Maintaining and Restoring Green Color of Salted Nozawana-2

Figure 7B:
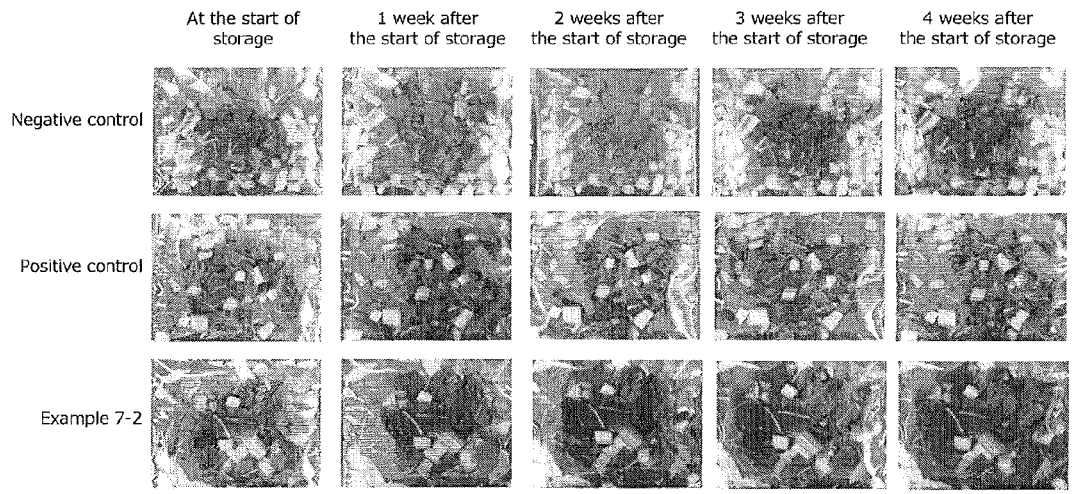
FIG. 7B is one exemplary photograph illustrating an effect for maintaining and restoring a green color of a vegetable in Example 7-2.

The storage test was performed in the same manner as in Example 6-2, except that the salted bracken was changed to the salted nozawana (manufactured by Taniguchi jozo Co., Ltd.). FIG. 7B shows salted nozawanas at the start of storage, 1 week after the start of storage, 2 weeks after the start of storage, 3 weeks after the start of storage, and 4 weeks after the start of storage. Table 8-2 shows measurement results obtained by means of the color difference meter (CR-400, manufactured by Konica Minolta, Inc.) at the start of storage, 2 weeks after the start of storage, and 4 weeks after the start of storage.

Note that, a positive control and a negative control were the same as in Example 6-2.

TABLE 8-2

| | At the start of photoirradiation | | | 2 weeks after the start of storage | | | 4 weeks after the start of storage | | |
|---|---|---|---|---|---|---|---|---|---|
| | L* | a* | b* | L* | a* | b* | L* | a* | b* |
| Negative control | 39.676 | −3.198 | 9.702 | 32.272 | −0.566 | 7.540 | 36.640 | −0.842 | 9.468 |
| Positive control | 35.610 | −5.772 | 7.292 | 32.476 | −5.290 | 6.648 | 34.788 | −4.542 | 5.768 |
| Ex. 7-2 | 37.662 | −6.208 | 8.644 | 33.410 | −5.246 | 7.016 | 34.580 | −4.516 | 5.898 |

As can be seen from FIG. 7B and Table 8-2, in Example 7-2 using the high-zinc-content yeast extract of the present invention, the salted nozawana had had a green color since the start of photoirradiation and had not discolored even 2 weeks and 4 weeks after the start of photoirradiation, which indicates an effect approximately equivalent to LEVELUP VG serving as the positive control. Note that, in the negative control, the salted nozawana had had a brown color and a high a* value since the start of photoirradiation.

Example 8-1

Evaluation of Effect for Maintaining and Restoring Green Color of Salted Cucumber-1

Figure 8A:
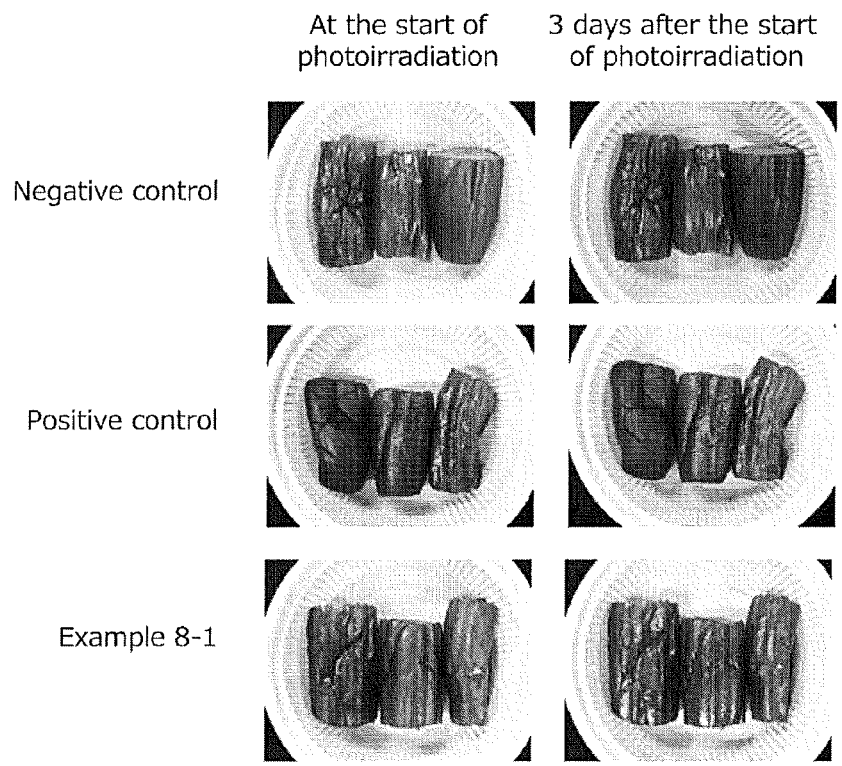
FIG. 8A is one exemplary photograph illustrating an effect for maintaining and restoring a green color of a vegetable in Example 8-1.

The photoirradiation test was performed in the same manner as in Example 6-1, except that the salted bracken was changed to a salted cucumber (manufactured by kissui Corporation). FIG. 8A shows salted cucumbers at the start of photoirradiation and 3 days after the start of photoirradiation. Table 9-1 shows measurement results obtained by means of the color difference meter (CR-400, manufactured by Konica Minolta, Inc.).

Note that, a positive control and a negative control were the same as in

Example 6-1

TABLE 9-1

| | At the start of photoirradiation | | | 3 days after the start of photoirradiation | | |
|---|---|---|---|---|---|---|
| | L* | a* | b* | L* | a* | b* |
| Negative control | 34.382 | −1.470 | 5.586 | 31.986 | −1.888 | 7.372 |
| Positive control | 37.644 | −5.556 | 5.994 | 29.780 | −6.904 | 7.962 |
| Ex. 8-1 | 35.458 | −5.476 | 5.060 | 32.238 | −7.676 | 8.326 |

As can be seen from FIG. 8A and Table 9-1, in Example 8-1 using the high-zinc-content yeast extract of the present invention, the salted cucumber had had a green color since the start of photoirradiation and had not discolored even 3 days after the start of photoirradiation, which indicates an effect approximately equivalent to LEVELUP VG serving as the positive control. Note that, in the negative control, the salted cucumber had had a brown color and a high a* value since the start of photoirradiation.

Example 8-2 Evaluation of Effect for Maintaining and Restoring Green Color of Salted Cucumber-2

Figure 8B:
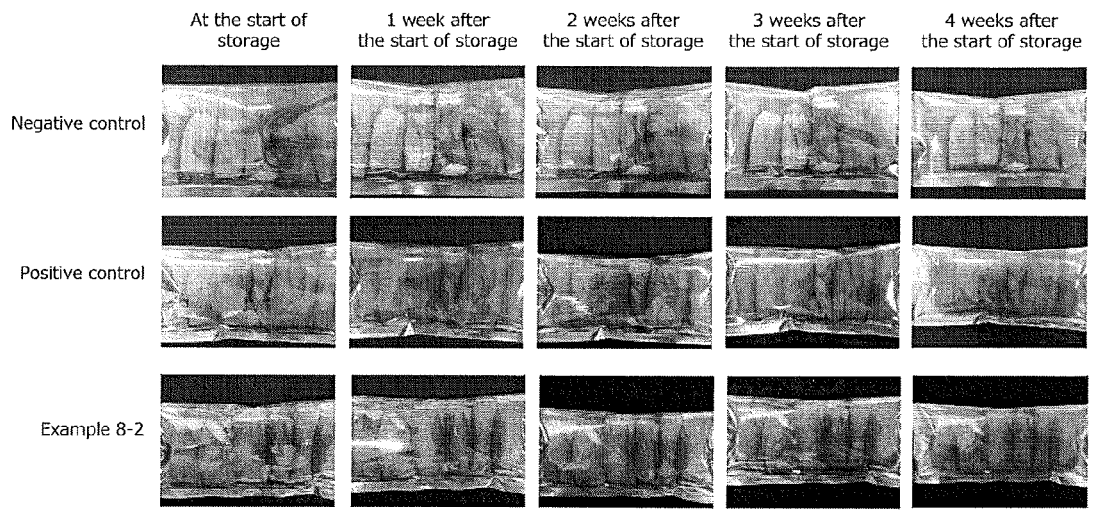
FIG. 8B is one exemplary photograph illustrating an effect for maintaining and restoring a green color of a vegetable in Example 8-2.

The storage test was performed in the same manner as in Example 6-2, except that the salted bracken was changed to the salted cucumber (manufactured by kissui Corporation). FIG. 8B shows salted cucumbers at the start of storage, 1 week after the start of storage, 2 weeks after the start of storage, 3 weeks after the start of storage, and 4 weeks after the start of storage. Table 9-2 shows measurement results obtained by means of the color difference meter (CR-400, manufactured by Konica Minolta, Inc.) at the start of storage, 2 weeks after the start of storage, and 4 weeks after the start of storage.

Note that, a positive control and a negative control were the same as in Example 6-2.

TABLE 9-2

|  | At the start of photoirradiation | | | 2 weeks after the start of photoirradiation | | | 4 weeks after the start of photoirradiation | | |
| --- | --- | --- | --- | --- | --- | --- | --- | --- | --- |
|  | L* | a* | b* | L* | a* | b* | L* | a* | b* |
| Negative control | 36.328 | −1.794 | 5.496 | 36.586 | −1.602 | 4.906 | 35.810 | −1.528 | 5.532 |
| Positive control | 36.670 | −6.214 | 5.184 | 36.346 | −6.208 | 5.096 | 37.492 | −6.004 | 5.276 |
| Ex. 8-2 | 35.176 | −5.128 | 4.300 | 34.634 | −5.534 | 4.526 | 36.448 | −5.480 | 5.126 |

As can be seen from FIG. 8B and Table 9-2, in Example 8-2 using the high-zinc-content yeast extract of the present invention, the salted cucumber had had a green color from the start of photoirradiation and had not discolored even 2 weeks and 4 weeks after the start of photoirradiation, which indicates an effect approximately equivalent to LEVELUP VG serving as the positive control. Note that, in the negative control, the salted cucumber had had a brown color and a high a* value since the start of photoirradiation.

Example 9

Evaluation of Effect for Maintaining and Restoring Green Color of Green Pepper

A commercially available green pepper is cut into pieces and added to a 1% by volume aqueous solution of brewed vinegar (manufactured by Mizkan Group Corporation), and then subjected to discoloration treatment by boiling at 65° C. to 70° C. for 30 min. Thereafter, a 2% (w/v) aqueous solution of the high-zinc-content yeast extract powder obtained in Example 3-8 was prepared. The discolored green pepper was transferred to and immersed into the aqueous solution overnight (16 hours), followed by draining with a colander to thereby separate the green pepper and the aqueous solution. The aqueous solution was boiled, to which the green pepper was added again. Then, the green pepper was boiled for 15 min, followed by draining with a colander and cooling with running water.

Figure 9:
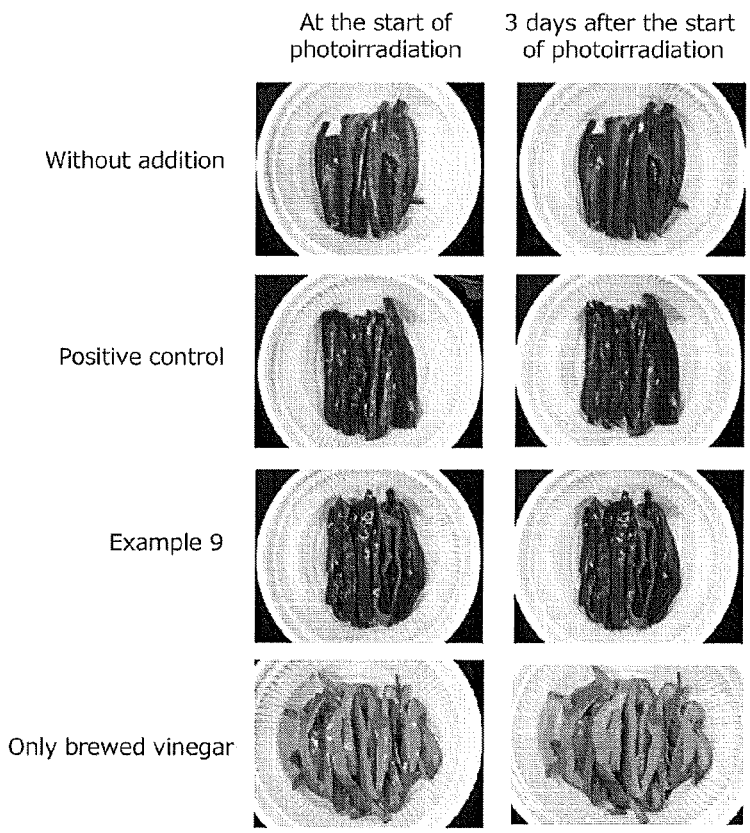
FIG. 9 is one exemplary photograph illustrating an effect for maintaining and restoring a green color of a vegetable in Example 9.

The resultant cool green pepper was photoirradiated at a light intensity of 600 luxes at 10° C., and observed at the start of photoirradiation and 3 days after the start of photoirradiation. FIG. 9 shows salted green peppers at each time. Table 10 shows measurement results obtained by means of the color difference meter (CR-400, manufactured by Konica Minolta, Inc.).

Note that, as a positive control, LEVELUP VG (mineral-containing lactobacillus, manufactured by Oriental Yeast Co., Ltd., see JP-B No. 4700497) was prepared to have the same zinc-content, followed by subjecting to the above-described test in the same manner. As a negative control, a green pepper which had not subjected to the discoloration treatment and had immersed into a solution containing neither the high-zinc-content yeast extract nor LEVELUP VG (hereinafter may be referred to as "without addition") was subjected to the test in the same manner. In addition, the green pepper which had treated only with the brewed vinegar (only discoloration treatment) was subjected to the test in the same manner

TABLE 10

|  | At the start of photoirradiation | | | 3 days after the start of photoirradiation | | |
| --- | --- | --- | --- | --- | --- | --- |
|  | L* | a* | b* | L* | a* | b* |
| Without addition | 39.250 | −11.378 | 15.306 | 38.398 | −6.526 | 14.832 |
| Positive control | 38.124 | −8.406 | 11.632 | 39.088 | −9.064 | 13.526 |
| Ex. 9 | 36.292 | −6.164 | 12.184 | 38.450 | −7.534 | 15.460 |
| Only brewed vinegar | 43.410 | −3.178 | 15.610 | 44.418 | −1.356 | 15.044 |

As can be seen from FIG. 9 and Table 10, in Example 9 using the high-zinc-content yeast extract of the present invention, the a* value was hardly changed even 3 days after the start of photoirradiation, that is, the green color was not discolored, which indicates an effect approximately equivalent to LEVELUP VG serving as the positive control. In contrast, in the case of without addition, the a* value was increased at 3 days after the start of photoirradiation.

A high-zinc-content yeast extract of the present invention contains zinc derived from a natural product in a high concentration, is excellent in water-solubility, and does not impair a flavor of food containing it, so that it can be suitably used as an oral or tube feeding composition (e.g., a liquid food or a beverage), a food material, various food additives (e.g., an agent for maintaining and restoring a green color of vegetables), and a food fermentation medium.

According to a method for producing a high-zinc-content yeast extract of the present invention, a high-zinc-content yeast extract which has a high zinc-elution rate from zinc-containing yeast can be efficiently produced.

What is claimed is:

1. A method for producing a high-zinc-content yeast extract, comprising:
    hot-water treating of zinc-containing yeast by suspending the zinc-containing yeast into hot-water having a temperature in a range from 60° C. to 120° C. so as to obtain a first suspension liquid, and separating a first solid component and a first liquid component of the first suspension liquid so as to obtain the first solid component; and
    extracting the high-zinc-content yeast extract by suspending the first solid component obtained in the hot-water treating step into a solution containing a carboxylic acid, a carboxylic acid salt, or both thereof so as to obtain a second suspension liquid, and separating a second solid component and a second liquid component of the second suspension liquid so as to obtain the second liquid component containing the high-zinc-content yeast extract.

2. The method for producing the high-zinc-content yeast extract according to claim 1, wherein a total amount of the carboxylic acid and the carboxylic acid salt is 0.2 mol or more relative to 1 mol of zinc contained in the yeast.

3. The method for producing the high-zinc-content yeast extract according to claim 1, wherein the carboxylic acid is a bivalent or higher carboxylic acid, and wherein the carboxylic acid salt is a bivalent or higher carboxylic acid salt.

4. The method for producing the high-zinc-content yeast extract according to claim 1, wherein the carboxylic acid is a trivalent carboxylic acid, and wherein the carboxylic acid salt is a trivalent carboxylic acid salt.

5. The method for producing the high-zinc-content yeast extract according to claim 1, wherein, in the hot-water treating step, a phosphoric acid salt is added to the hot-water.

6. A high-zinc-content yeast extract, comprising:
0.4% by mass or more of zinc derived from a yeast fungus body,
wherein a turbidity is 0.10 or less in terms of absorbance at a wavelength of 660 nm (O. D. 660) when 1 g of the high-zinc-content yeast extract is dissolved or dispersed into 100 mL of water.

7. The high-zinc-content yeast extract according to claim 6 produced by a method for producing a high-zinc-content yeast extract, the method comprising:
hot-water treating of zinc-containing yeast by suspending the zinc-containing yeast into hot-water having a temperature in a range from 60° C. to 120° C. so as to obtain a first suspension liquid, and separating a first solid component and a first liquid component of the first suspension liquid so as to obtain the first solid component; and
extracting the high-zinc-content yeast extract by suspending the first solid component obtained in the hot-water treating step into a solution containing a carboxylic acid, a carboxylic acid salt, or both thereof so as to obtain a second suspension liquid, and separating a second solid component and a second liquid component of the second suspension liquid so as to obtain the second liquid component containing the high-zinc-content yeast extract.

8. Food, comprising:
a high-zinc-content yeast extract which comprises:
0.4% by mass or more of zinc derived from a yeast fungus body,
wherein a turbidity is 0.10 or less in terms of absorbance at a wavelength of 660 nm (O. D. 660) when 1 g of the high-zinc-content yeast extract is dissolved or dispersed into 100 mL of water.

9. An agent for maintaining and restoring a green color of vegetables, comprising:
a high-zinc-content yeast extract which comprises:
0.4% by mass or more of zinc derived from a yeast fungus body,
wherein a turbidity is 0.10 or less in terms of absorbance at a wavelength of 660 nm (O. D. 660) when 1 g of the high-zinc-content yeast extract is dissolved or dispersed into 100 mL of water.

10. The food according to claim 8,
wherein the high-zinc-content yeast extract is produced by a method comprising:
hot-water treating of zinc-containing yeast by suspending the zinc-containing yeast into hot-water having a temperature in a range from 60° C. to 120° C. so as to obtain a first suspension liquid, and separating a first solid component and a first liquid component of the first suspension liquid so as to obtain the first solid component; and
extracting the high-zinc-content yeast extract by suspending the first solid component obtained in the hot-water treating step into a solution containing a carboxylic acid, a carboxylic acid salt, or both thereof so as to obtain a second suspension liquid, and separating a second solid component and a second liquid component of the second suspension liquid so as to obtain the second liquid component containing the high-zinc-content yeast extract.

11. The agent for maintaining and restoring a green color of vegetables according to claim 9,
wherein the high-zinc-content yeast extract is produced by a method comprising:
hot-water treating of zinc-containing yeast by suspending the zinc-containing yeast into hot-water having a temperature in a range from 60° C. to 120° C. so as to obtain a first suspension liquid, and separating a first solid component and a first liquid component of the first suspension liquid so as to obtain the first solid component; and
extracting the high-zinc-content yeast extract by suspending the first solid component obtained in the hot-water treating step into a solution containing a carboxylic acid, a carboxylic acid salt, or both thereof so as to obtain a second suspension liquid, and separating a second solid component and a second liquid component of the second suspension liquid so as to obtain the second liquid component containing the high-zinc-content yeast extract.

* * * * *